(12) United States Patent
Kravtchenko

(10) Patent No.: US 7,799,092 B2
(45) Date of Patent: Sep. 21, 2010

(54) COMPOSITION FOR SIMULTANEOUSLY BLEACHING AND DYEING KERATIN FIBERS, COMPRISING AT LEAST ONE ANIONIC OR NONIONIC DIRECT DYE AND AT LEAST ONE ASSOCIATIVE POLYMER

(75) Inventor: Sylvain Kravtchenko, Shanghai (CN)

(73) Assignee: L'Oreal S.A., Paris (FR)

( * ) Notice: Subject to any disclaimer, the term of this patent is extended or adjusted under 35 U.S.C. 154(b) by 87 days.

(21) Appl. No.: 11/476,875

(22) Filed: Jun. 29, 2006

(65) Prior Publication Data

US 2007/0033744 A1    Feb. 15, 2007

Related U.S. Application Data

(60) Provisional application No. 60/696,509, filed on Jul. 6, 2005.

(30) Foreign Application Priority Data

Jun. 29, 2005    (FR) .................................. 05 51812

(51) Int. Cl.
   *A61Q 5/10*    (2006.01)
(52) U.S. Cl. ....................... 8/405; 8/406; 8/415; 8/435; 8/437; 8/455; 8/456; 8/463; 8/464; 8/617; 8/552; 8/554; 8/637.1; 8/107; 8/111
(58) Field of Classification Search .................... 8/405, 8/406, 415, 435, 437, 455, 456, 463, 464, 8/617, 552, 554, 637.1, 107, 111
See application file for complete search history.

(56) References Cited

U.S. PATENT DOCUMENTS

| 3,578,387 | A | 5/1971 | Zviak et al. |
|---|---|---|---|
| 3,915,921 | A | 10/1975 | Schlatzer, Jr. |
| 4,509,949 | A | 4/1985 | Huang et al. |
| 4,823,985 | A | 4/1989 | Grollier et al. |
| 5,595,197 | A | 1/1997 | Samain et al. |
| 5,688,291 | A | 11/1997 | Said et al. |
| 5,792,221 | A | 8/1998 | Lagrange et al. |
| 6,379,401 | B1 | 4/2002 | Legrand et al. |
| 6,537,328 | B1 | 3/2003 | Lang et al. |
| 6,540,791 | B1 * | 4/2003 | Dias ............... 8/111 |
| 7,223,294 | B2 | 5/2007 | Desenne et al. |
| 2002/0004957 | A1 | 1/2002 | Imperial |
| 2002/0102225 | A1 | 8/2002 | Hess et al. |
| 2003/0124079 | A1 | 7/2003 | Mougin et al. |
| 2003/0172473 | A1 * | 9/2003 | Desenne et al. ........... 8/405 |
| 2003/0192134 | A1 | 10/2003 | Desenne et al. |
| 2004/0141943 | A1 | 7/2004 | Mougin et al. |
| 2004/0181883 | A1 | 9/2004 | Legrand et al. |
| 2004/0205901 | A1 | 10/2004 | Cottard et al. |
| 2005/0050650 | A1 | 3/2005 | Rollat-Corvol et al. |
| 2005/0183212 | A1 | 8/2005 | Plos |
| 2005/0191251 | A1 | 9/2005 | Kravtchenko et al. |
| 2005/0257328 | A1 | 11/2005 | Sallwey et al. |
| 2006/0185098 | A1 | 8/2006 | Kravtchenko et al. |
| 2006/0191079 | A1 | 8/2006 | Kravtchenko et al. |
| 2006/0191080 | A1 | 8/2006 | Kravtchenko et al. |

FOREIGN PATENT DOCUMENTS

| DE | 203 03 559 U1 | 10/2003 |
|---|---|---|
| EP | 0 173 109 B1 | 3/1986 |
| EP | 0 216 479 B1 | 4/1987 |
| EP | 1048 289 A2 * | 11/2000 |
| FR | 2 586 913 A1 | 3/1987 |
| FR | 2 692 572 A1 | 12/1993 |
| FR | 2 713 926 A1 | 6/1995 |
| FR | 2 773 478 A1 | 7/1999 |
| FR | 2 788 976 A1 | 8/2000 |
| FR | 2 811 993 A1 | 1/2002 |
| FR | 2 820 032 A1 | 8/2002 |
| FR | 2 833 833 A1 | 6/2003 |
| FR | 2 857 587 A1 | 1/2005 |
| FR | 2 864 444 A1 | 7/2005 |
| FR | 2 865 396 A1 | 7/2005 |
| FR | 2 878 741 A1 | 6/2006 |
| FR | 2 878 742 A1 | 6/2006 |
| FR | 2 878 743 A2 | 6/2006 |
| GB | 859 550 | 1/1961 |
| WO | WO 98/44012 | 10/1998 |
| WO | WO 01/28508 A1 | 4/2001 |
| WO | WO 02/074270 A1 | 9/2002 |
| WO | WO 2004/078150 A1 | 9/2004 |

OTHER PUBLICATIONS

English Abstract of the Patent No. EP 1048 289 A2.*
French Search Report for FR 0551812, dated Feb. 17, 2006.
French Search Report for FR 0551813, dated Feb. 23, 2006.
G. Fonnum et al., "Associative thickeners. Part I: Synthesis, rheology and aggregation behavior," Colloid & Polymer Science, vol. 271, No. 4, pp. 380-389 (1993).
Co-pending U.S. Appl. No. 11/476,814 Inventor: Sylvain Kravtchenko filed Jun. 29, 2006.
Office Action mailed Mar. 19, 2008, in co-pending U.S. Appl. No. 11/476,814.
Final Office Action mailed Dec. 2, 2008, in co-pending U.S. Appl. No. 11/476,814.
Advisory Action mailed Feb. 10, 2009, in co-pending U.S. Appl. No. 11/476,814.

* cited by examiner

*Primary Examiner*—Eisa B Eihilo
(74) *Attorney, Agent, or Firm*—Finnegan, Henderson, Farrabow, Garrett & Dunner LLP

(57) ABSTRACT

The disclosure provides compositions for simultaneously bleaching and dyeing keratin fibers, comprising at least one direct dye chosen from anionic and nonionic dyes, with the exception of 7-(6'-methylphenylazo)-1-acetamido-3,6-disulfo-8-hydroxynaph-thalene, ortho-nitroanilines substituted meta to the amino group, quinoline and quinoline derivatives, and addition salts thereof, at least one associative polymer, at least one peroxygenated salt and at least one alkaline agent, to processes for simultaneously bleaching and dyeing keratin fibers using the compositions, and to uses of the compositions for simultaneously bleaching and dyeing keratin fibers. The compositions are suitable for dark hair. They are easy to use and can produce chromatic and fast coloration.

23 Claims, No Drawings

COMPOSITION FOR SIMULTANEOUSLY BLEACHING AND DYEING KERATIN FIBERS, COMPRISING AT LEAST ONE ANIONIC OR NONIONIC DIRECT DYE AND AT LEAST ONE ASSOCIATIVE POLYMER

This application claims benefit of U.S. Provisional Application No. 60/696,509, filed Jul. 6, 2005, the contents of which are incorporated herein by reference. This application also claims benefit of priority under 35 U.S.C. §119 to French Patent Application No. FR 05 51812, filed Jun. 29, 2005, the contents of which are also incorporated herein by reference.

The present disclosure provides compositions for simultaneously bleaching and dyeing keratin fibers, including human keratin fibers such as the hair.

When a person wishes to radically change hair color, for example, when he or she wishes to obtain a color lighter than his or her original color, it is often necessary to perform bleaching and optionally dyeing of the hair. Several methods are available to do this.

The first method involves using lightening products based on aqueous ammonia and hydrogen peroxide. These products may optionally contain dyes allowing the hair to be simultaneously lightened and dyed. However, the lightening performance of these products remains limited, in particular for applications on natural and/or dyed dark-colored hair.

The second method involves applying to the hair a lightening composition based on peroxygenated salts such as persulfates and alkaline agents to which hydrogen peroxide has been added at the time of use, in order to obtain greater lightening. This type of product is satisfactory and more suitable for dark hair, but gives access to a very limited range of tints. It then may be necessary to correct the shade obtained by applying to the hair a coloring product in a second stage. This two-stage process has the drawback of taking a long time.

To overcome this drawback, it has been proposed, in U.S. Pat. No. 5,688,291, and patent publications WO 02/074270 and DE 203 03 559, to add dyes to these lightening products, such as anthraquinone, azo, triarylmethane, thiazine, quinone and nitro direct dyes, some of which are stable in these highly oxidative media. This method allows hair fibers to be simultaneously dyed and bleached. Since the level of lightening is substantial, it is suitable for natural and/or dyed dark-colored hair. However, these products have the drawback of being in the form of powders that are volatile and thus of reduced practicality.

The present disclosure provides novel compositions for simultaneously bleaching and dyeing keratin fibers, including human keratin fibers such as the hair, which are suitable, for example, for dark-colored hair, which are easy to use, and/or which can produce chromatic and fast colorations.

In one aspect, the present disclosure provides compositions for simultaneously bleaching and dyeing keratin fibers, comprising:
- at least one direct dye chosen from anionic and nonionic dyes, with the exception of 7-(6'-methylphenylazo)-1-acetamido-3,6-disulfo-8-hydroxynaphthalene, ortho-nitroanilines substituted meta to the amino group, quinoline, quinoline derivatives, and addition salts thereof;
- at least one associative polymer;
- at least one peroxygenated salt; and
- at least one alkaline agent.

The compositions disclosed herein are also suitable for simultaneously bleaching and dyeing dark hair. They are easy to use and may produce a chromatic coloration. Furthermore, with suitable concentrations of dyes, a wide range of colors and tints may be obtained.

This coloration may withstand the various attacking factors to which the hair may be subjected, such as shampoo, rubbing, light, bad weather, sweat, and/or permanent reshaping. It may also be powerful, aesthetic and/or, furthermore, sparingly selective, i.e., produce small differences in color between different parts of a hair or of a head of hair which are differently sensitized.

Moreover, when the compositions are in powder form, mixtures with an aqueous composition comprising hydrogen peroxide may be easier to prepare than mixtures with standard powders.

The present disclosure also relates to processes for simultaneously bleaching and dyeing keratin fibers using the compositions disclosed herein, and also multi-compartment devices for performing the processes.

The present disclosure also relates to the use of the compositions disclosed herein for simultaneously bleaching and dyeing keratin fibers.

Anionic Direct Dyes

Anionic direct dyes that may be used herein include, but are not limited to, acidic nitro direct dyes, acidic azo dyes, acidic azine dyes, acidic triarylmethane dyes, acidic indoamine dyes, and acidic natural dyes.

In at least one embodiment, the anionic direct dyes that are useful in the present disclosure may be chosen from the following compounds:

| | |
|---|---|
| (C.I. 45380) | Acid Red 87 |
| (C.I. 10316) | Sodium salt of 2,4-dinitro-1-naphthol-7-sulfonic acid |
| (C.I. 10383) | Acid Orange 3 |
| (C.I. 13015) | Acid Yellow 9/Food Yellow 2 |
| (C.I. 14780) | Direct Red 45/Food Red 13 |
| (C.I. 13711) | Acid Black 52 |
| (C.I. 13065) | Acid Yellow 36 |
| (C.I. 14700) | Sodium salt of 1-hydroxy-2-(2',4'-xylyl-5-sulfonatoazo)naphthalene-4-sulfonic acid/Food Red 1 |
| (C.I. 14720) | Acid Red 14/Food Red 3/Mordant Blue 79 |
| (C.I. 14805) | Acid Brown 4 |
| (C.I. 15510) | Acid Orange 7/Pigment Orange 17/Solvent Orange 49 |
| (C.I. 15985) | Food Yellow 3/Pigment Yellow 104 |
| (C.I. 16185) | Acid Red 27/Food Red 9 |
| (C.I. 16230) | Acid Orange 10/Food Orange 4 |
| (C.I. 16250) | Acid Red 44 |
| (C.I. 17200) | Acid Red 33/Food Red 12 |
| (C.I. 15685) | Acid Red 184 |
| (C.I. 19125) | Acid Violet 3 |
| (C.I. 18055) | Sodium salt of 1-hydroxy-2-(4'-acetamidophenylazo)-8-acetamidonaphthalene-3,6-disulfonic acid/Acid Violet 7/Food Red 11 |
| (C.I. 18130) | Acid Red 135 |
| (C.I. 19130) | Acid Yellow 27 |
| (C.I. 19140) | Acid Yellow 23/Food Yellow 4 |
| (C.I. 20170) | 4'-(Sulfonato-2",4"-dimethyl)bis(2,6-phenylazo)-1,3-dihydroxybenzene/Acid Orange 24 |
| (C.I. 20470) | Sodium salt of 1-amino-2-(4'-nitrophenylazo)-7-phenylazo-8-hydroxynaphthalene-3,6-disulfonic acid/Acid Black 1 |
| (C.I. 23266) | (4-((4-Methylphenyl)sulfonyloxy)phenylazo)-2,2'-dimethyl-4-((2-hydroxy-5,8-disulfonato)naphthylazo)biphenyl/Acid Red 111 |
| (C.I. 27755) | Food Black 2 |
| (C.I. 25440) | 1-(4'-Sulfonatophenylazo)-4-((2"-hydroxy-3"-acetylamino-6",8"-disulfonato)naphthylazo)-6-sulfonatonaphthalene (tetrasodium salt)/Food Black 1 |
| (C.I. 42080) | 4-β-Hydroxyethylamino-3-nitrobenzenesulfonic acid |
| (C.I. 42090) | Acid Blue 9 |
| (C.I. 60730) | Acid Violet 43 |
| (C.I. 61570) | Acid Green 25 |
| (C.I. 62045) | Sodium salt of 1-amino-4-cyclohexylamino-9,10-anthraquinone-2-sulfonic acid/Acid Blue 62 |

-continued

| | |
|---|---|
| (C.I. 62105) | Acid Blue 78 |
| (C.I. 14710) | Sodium salt of 4-hydroxy-3-((2-methoxyphenyl)azo)-1-naphthalenesulfonic acid/Acid Red 4 |
| | 2-Piperidino-5-nitrobenzenesulfonic acid |
| | 2-(4'-N,N-(2''-Hydroxyethyl)amino-2'-nitro)-anilinethanesulfonic acid |
| | 4-β-Hydroxyethylamino-3-nitrobenzenesulfonic acid |
| (C.I. 42640) | Acid Violet 49 |
| (C.I. 42080) | Acid Blue 7 |
| — | Acid Blue 156 |
| — | Acid Blue 317 |
| (C.I. 58005) | Sodium salt of 1,2-dihydroxy-3-sulfoanthraquinone/Mordant Red 3 |
| (C.I. 62055) | Sodium salt of 1-amino-9,10-dihydro-9,10-dioxo-4-(phenylamino)-2-anthracenesulfonic acid/Acid Blue 25 |
| (C.I. 14710) | Sodium salt of 4-hydroxy-3-((2-methoxyphenyl)azo)-1-naphthalenesulfonic acid/Acid Red 4 |

Many of these dyes are described in the Color Index published by The Society of Dyers and Colorists, P.O. Box 244, Perkin House, 82 Grattan Road, Bradford, Yorkshire, BD1 2JB, England.

In at least one embodiment, the anionic direct dyes that are used are the dyes listed in the Color Index under the code:
C.I. 58005 (monosodium salt of 1,2-dihydroxy-9,10-anthraquinone-3-sulfonic acid),
C.I. 60730 (monosodium salt of 2-[(9, 10-dihydro-4-hydroxy-9,10-dioxo-1-anthracenyl)amino]-5-methylbenzenesulfonic acid),
C.I. 15510 (monosodium salt of 4-[(2-hydroxy-1-naphthyl)azo]benzenesulfonic acid),
C.I. 15985 (disodium salt of 6-hydroxy-5-[(4-sulfophenyl)azo]-2-naphthalenesulfonic acid),
C.I. 17200 (disodium salt of 5-amino-4-hydroxy-3-(phenylazo)-2,7-naphthalenedisulfonic acid),
C.I. 20470 (disodium salt of 1-amino-2-(4'-nitrophenylazo)-7-phenylazo-8-hydroxynaphthalene-3,6-disulfonic acid),
C.I. 42090 (disodium salt of N-ethyl-N-[4-[[4-[ethyl(3-sulfophenyl)methyl]amino]phenyl](2-sulfophenyl)methylene]-2,5-cyclohexadien-1-ylidene]-3-sulfobenzenemethanaminium hydroxide, inner salt), and
C.I. 61570 (disodium salt of 2,2'-[(9,10-dihydro-9,10-dioxo-1,4-anthracenediyl)diimino]bis[5-methyl]benzenesulfonic acid).

In another embodiment, the anionic direct dyes that may be used in the present disclosure include, but are not limited to, the following compounds:
4-(β-hydroxyethyl)amino-3-nitrobenzenesulfonic acid;
4-N-ethylamino-3-nitrobenzoic acid;
2-piperidino-5-nitrobenzoic acid;
4-amino-2-nitrodiphenylamine-2'-carboxylic acid;
4-amino-4'-dimethylamino-2-nitrodiphenylamine-2'-carboxylic acid; and
3-oxo-6-hydroxy-9-carboxyphenylxanthylium acid.

Nonionic Direct Dyes

Nonionic direct dyes that may be used in the presently disclosed compositions include, but are not limited to, nonionic nitrobenzene dyes and nonionic azo, azomethine, methine, anthraquinone, naphthoquinone, benzoquinone, phenothiazine, indigoid, xanthene, phenanthridine, phthalocyanin, and triarylmethane-based dyes, alone or as mixtures.

The nonionic direct dyes may be chosen, for example, from red or orange nitrobenzene dyes, for example from the following compounds:

1-hydroxy-3-nitro-4-N-(γ-hydroxypropyl)aminobenzene,
N-(β-hydroxyethyl)amino-3-nitro-4-aminobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene, and
2-nitro-4'-hydroxydiphenylamine.

They may also be chosen from yellow and green-yellow nitrobenzene direct dyes, including, but not limited to:
1-(β-hydroxyethyl)amino-2-methoxy-4-nitrobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

They may also be chosen from blue or violet nitrobenzene direct dyes, including, but not limited to:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene, and
2-nitro-para-phenylenediamines of the formula:

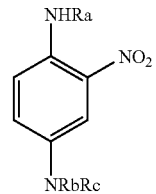

wherein:
Rb is chosen from a $C_1$-$C_4$ alkyl radical, a β-hydroxyethyl radical, a β-hydroxypropyl radical, and a γ-hydroxypropyl radical;
Ra and Rc, which may be identical or different, are each chosen from β-hydroxyethyl, β-hydroxypropyl, γ-hydroxypropyl and β,γ-dihydroxypropyl radicals, wherein at least one of the radicals Rb, Rc or Ra is a γ-hydroxypropyl radical, and wherein Rb and Rc are not both a β-hydroxyethyl radical when Ra is a γ-hydroxypropyl radical. Such compounds are described in, for example, French patent FR 2 692 572.

Nonionic dyes that may be used herein also include, but are not limited to, the following dyes: Disperse Orange 3; Disperse Red 17; Disperse Violet 4; Disperse Violet 8; Disperse Blue 1; Disperse Red 15; Solvent Violet 13; Solvent Violet 11; Disperse Blue 3; Disperse Blue 7; Disperse Red 11; Natural Brown 7; Disperse Black 9; Disperse Violet 15; Natural Orange 6; 2-hydroxy-3-methoxy-1,4-naphthoquinone; 3-hydroxy-2-methyl-1,4-naphthoquinone or phthiocol; 3,6-dihydroxy-5-methoxy-p-toluquinone or spinulosin; and HC Blue 14.

In at least one embodiment, the nonionic dyes are chosen from 1-hydroxy-3-nitro-4-N-(γ-hydroxypropyl)aminobenzene; N-(β-hydroxyethyl)amino-3-nitro-4-aminobenzene; 1-hydroxy-3-nitro-4-N-(β-hydroxyethyl)aminobenzene; 1,4-diamino-2-nitrobenzene; 1-amino-2-nitro-4-methylaminobenzene; N-(β-hydroxyethyl)-2-nitro-para-phenylenediamine; 2-nitro-4-aminodiphenylamine; 1-amino-3-nitro-6-hydroxybenzene; 1-(β-aminoethyl)amino-2-nitro-4-(β-hydroxyethyloxy)benzene; 1-(β,γ-dihydroxypropyl)oxy-3-nitro-4-(β-hydroxyethyl)aminobenzene; 1-hydroxy-3-nitro-4-aminobenzene; 1-hydroxy-2-amino-4,6-dinitrobenzene; 1-methoxy-3-nitro-4-(β-hydroxyethyl)aminobenzene; 2-nitro-4'-hydroxy-diphenylamine; 1-(β-hydroxyethyl)amino-2-methoxy-4-nitrobenzene; 1-amino-2-nitro-6-methylbenzene; 1-(β-hydroxyethyl)amino-2-hydroxy-4-nitrobenzene; N-(β-hydroxyethyl)-2-nitro-4-trifluoromethylaniline; 4-(β-hydroxyethyl)amino-3-nitrochlorobenzene; 4-β-hydroxyethyl)amino-3-nitromethylbenzene; 4-(β,γ-dihydroxypropyl)amino-3-nitrotrifluoromethyl-benzene; 1-(β-ureidoethyl)amino-4-nitrobenzene; 1-hydroxy-2-amino-5-nitrobenzene; 1-amino-2-[tris(hydroxymethyl)methyl] amino-5-nitrobenzene; 1-(β-hydroxyethyl)amino-2-nitrobenzene; 4-(β-hydroxyethyl)amino-3-nitrobenzamide; 1-(β-hydroxyethyl)amino-4-N,N-bis(β-hydroxyethyl)amino-2-nitrobenzene; 1-(γ-hydroxypropyl)amino-4-N,N-bis(β-hydroxy-ethyl)amino-2-nitrobenzene; 1-(β-hydroxyethyl) amino-4-(N-methyl-N-β-hydroxyethyl)amino-2-nitrobenzene; 1-(β-hydroxyethyl)amino-4-(N-ethyl-N-β-hydroxyethyl)amino-2-nitrobenzene; 1-(β,γ-dihydroxypropyl)amino-4-(N-ethyl-N-β-hydroxyethyl) amino-2-nitro-benzene; Disperse Orange 3; Disperse Red 17; Disperse Violet 4; Disperse Violet 8; Disperse Blue 1; Disperse Red 15; Solvent Violet 13; Solvent Violet 11; Disperse Blue 3; Disperse Blue 7; Disperse Red 11; Natural Brown 7; Disperse Black 9; Disperse Violet 15; Natural Orange 6; 2-hydroxy-3-methoxy-1,4-naphthoquinone; 3-hydroxy-2-methyl-1,4-naphthoquinone or phthiocol; 3,6-dihydroxy-5-methoxy-p-toluquinone or spinulosin; and HC Blue 14.

In at least one embodiment, the concentration of the anionic and/or nonionic dyes in the compositions may range from 0.0001% to 10% by weight, for example, from 0.001% to 8% or from 0.01% to 5% by weight, relative to the total weight of the composition.

Associative Polymers

Associative polymers, as defined herein, are water-soluble polymers capable, in an aqueous medium, of reversibly associating with each other or with other molecules. Their chemical structure comprises hydrophilic regions and hydrophobic regions characterized by at least one fatty chain.

The associative polymers according to the present disclosure may be anionic, cationic, amphoteric or nonionic polymers. In at least one embodiment, the associative polymers are cationic or nonionic.

Anionic Associative Polymers

Anionic associative polymers useful herein include, but are not limited to:

(I) polymers comprising at least one hydrophilic unit and at least one fatty-chain allyl ether unit, such as polymers with hydrophilic units comprising an ethylenic unsaturated anionic monomer, for example, a vinylcarboxylic acid, an acrylic acid, a methacrylic acid, and mixtures thereof, the fatty-chain allyl ether unit of which corresponds to the monomer of formula (I) below:

$$CH_2=CR'CH_2OB_nR \qquad (I)$$

wherein R' is chosen from H and $CH_3$, B is an ethyleneoxy radical, n is zero or an integer ranging from 1 to 100, and R is a hydrocarbon-based radical chosen from alkyl, arylalkyl, aryl, alkylaryl, and cycloalkyl radicals, said radical having from 8 to 30 carbon atoms, such as 10 to 24 carbon atoms or 12 to 18 carbon atoms. In at least one embodiment of formula (I), R' is H, n is 10, and R is a stearyl ($C_{18}$) radical.

Anionic associative polymers of this type are described and prepared, for example, according to an emulsion polymerization process, in patent EP 0 216 479.

In at least one embodiment, the anionic associative polymers are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which may be a copolymerizable unsaturated polyethylenic monomer, for example, diallyl phthalate, allyl (meth)acrylate, divinylbenzene, (poly)ethylene glycol dimethacrylate, or methylenebisacrylamide.

The latter polymers, include, but are not limited to, crosslinked terpolymers of methacrylic acid, of ethyl acrylate and of polyethylene glycol (10 EO) stearyl alcohol ether (Steareth-10), such as those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10);

(II) polymers comprising at least one hydrophilic unit of unsaturated olefinic carboxylic acid type, and at least one hydrophobic unit of ($C_{10}$-$C_{30}$)alkyl ester of unsaturated carboxylic acid type.

In at least one embodiment, these polymers are chosen from those in which the hydrophilic unit of unsaturated olefinic carboxylic acid type is a monomer of formula (II):

$$CH_2=\underset{R_1}{\underset{|}{C}}-\underset{O}{\overset{\parallel}{C}}-OH \qquad (II)$$

wherein $R_1$ is chosen from H, $CH_3$, and $C_2H_5$, i.e., the monomer units are chosen from acrylic acid, methacrylic acid, and ethacrylic acid units, and wherein the hydrophobic unit of ($C_{10}$-$C_{30}$) alkyl ester of unsaturated carboxylic acid type is a monomer of formula (III):

$$CH_2=\underset{R_2}{\underset{|}{C}}-\underset{O}{\overset{\parallel}{C}}-OR_3 \qquad (III)$$

wherein $R_2$ is chosen from H, $CH_3$, and $C_2H_5$, i.e., the monomer units are chosen from acrylate, methacrylate, and ethacrylate units, for example, $R_2$ is H (acrylate units) or $CH_3$ (methacrylate units), and $R_3$ is a $C_{10}$-$C_{30}$ radical, for example, a $C_{12}$-$C_{22}$ alkyl radical.

($C_{10}$-$C_{30}$) alkyl esters of unsaturated carboxylic acids that may be used include, but are not limited to, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate, and dodecyl methacrylate.

Anionic polymers of this type are described and may be prepared, for example, according to U.S. Pat. Nos. 3,915,921 and 4,509,949.

In at least one embodiment, anionic associative polymers of this type that may be used include polymers formed from a monomer mixture comprising:

(i) acrylic acid, (ii) an ester of formula (III) described above wherein $R_2$ is chosen from H and $CH_3$, and $R_3$ is an alkyl radical having from 12 to 22 carbon atoms, and (iii) a copolymerizable polyethylenic unsaturated monomer crosslinking agent, for example, diallyl phthalate, allyl (meth)acrylate, divinylbenzene, (poly)ethylene glycol dimethacrylate, and methylenebisacrylamide.

Anionic associative polymers of this type that may be used include those having from 60% to 95% by weight of acrylic acid (hydrophilic unit), from 4% to 40% by weight of $C_{10}$-$C_{30}$ alkyl acrylate (hydrophobic unit), and from 0% to 6% by weight of a crosslinking polymerizable monomer, and those having from 96% to 98% by weight of acrylic acid (hydrophilic unit), from 1% to 4% by weight of $C_{10}$-$C_{30}$ alkyl acrylate (hydrophobic unit), and from 0.1% to 0.6% by weight of a crosslinking polymerizable monomer such as those described above.

Examples of the polymers listed above include the products sold by the company Goodrich under the trade names Pemulen TR1®, Pemulen TR2®, and Carbopol 1382®, for example, Pemulen TR1®, and the product sold by the company SEPPIC under the name Coatex SX®;

(III) maleic anhydride/C30-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies;

(IV) acrylic terpolymers comprising:

(a) from 20% to 70% by weight of a carboxylic acid containing α,β-monoethylenic unsaturation, (b) from 20% to 80% by weight of a non-surfactant monomer containing α,β-monoethylenic unsaturation other than the carboxylic acid in (a), (c) from 0.5% to 60% by weight of a nonionic monourethane which is the product of reaction of a monohydric surfactant with a monoisocyanate containing monoethylenic unsaturation, such as those described in patent application Eβ-A-0 173 109, for example, the terpolymer described in Example 3 (a methacrylic acid/methyl acrylate/behenyl alcohol dimethyl-metaisopropenylbenzylisocyanate ethoxylated (40 EO) terpolymer, as an aqueous 25% dispersion); and (V) copolymers comprising carboxylic acid monomers having α,β-monoethylenic unsaturation and ester monomers of a carboxylic acid having α,β-monoethylenic unsaturation, and of an oxyalkylenated fatty alcohol.

In at least one embodiment, these compounds further comprise as monomer an ester of a carboxylic acid containing α,β-monoethylenic unsaturation and of a $C_1$-$C_4$ alcohol.

Aculyn 22® sold by the company Rohm & Haas, which is a methacrylic acid/ethyl acrylate/stearyl methacrylate oxyalkylenated terpolymer, is an example of a compound of this type.

Cationic Associative Polymers

Cationic associative polymers that may be used herein include, but are not limited to:

(I) cationic associative polyurethanes described in patent application FR-00/09609 (now published as FR 2 811 993) of formula (IV):

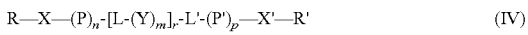

$$R\text{—}X\text{—}(P)_n\text{-}[L\text{-}(Y)_m]_r\text{-}L'\text{-}(P')_p\text{—}X'\text{—}R' \quad (IV)$$

wherein:

R and R', which may be identical or different, are each chosen from a hydrophobic group and a hydrogen atom;

X and X', which may be identical or different, are each chosen from a group comprising an amine function optionally bearing a hydrophobic group and a group L";

L, L' and L", which may be identical or different, each are a group derived from a diisocyanate;

P and P', which may be identical or different, each are a group comprising an amine function optionally bearing a hydrophobic group;

Y is a hydrophilic group;

r is an integer ranging from 1 to 100, for example, from 1 to 50 and from 1 to 25; and n, m and p each range, independently of each other, from 0 to 1000;

the molecule containing at least one protonated or quaternized amine function and at least one hydrophobic group.

In one embodiment, the only hydrophobic groups of these polyurethanes are the groups R and R' at the chain ends.

In at least one embodiment, the cationic associative polyurethanes correspond to formula (IV) above wherein:

R and R' both independently are a hydrophobic group,

X and X' each independently are a group L", n and p each independently range from 1 to 1000, and L, L', L", P, P', Y, r, and m are as described above.

In other embodiments, the cationic associative polyurethanes correspond to formula (IV) above wherein:

R and R' both independently are a hydrophobic group,

X and X' each independently are a group L", n and p each are 0, and

L, L', L", Y, r, and m are as described above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e., compounds of the formula RQ or R'Q, wherein R and R' are as defined above and Q is a leaving group such as a halide, a sulfate, etc.

In yet other embodiments, the cationic associative polyurethanes correspond to formula (IV) above wherein:

R and R' both independently are a hydrophobic group,

X and X' both independently are a group comprising a quaternary amine, n and p are zero, and L, L', Y, r and m are as described above.

The number-average molecular mass of the cationic associative polyurethanes may range from 400 to 500,000, for example, from 1000 to 400,000 or from 1000 to 300,000.

The expression "hydrophobic group" means a radical or polymer comprising a saturated or unsaturated, linear or branched hydrocarbon-based chain, which may comprise one or more heteroatoms such as P, O, N, and S, or a radical containing a perfluoro or silicone chain. When the hydrophobic group is a hydrocarbon-based radical, it comprises at least 10 carbon atoms, for example, from 10 to 30 carbon atoms, from 12 to 30 carbon atoms, or from 18 to 30 carbon atoms.

In at least one embodiment, the hydrocarbon-based group is derived from a monofunctional compound.

In some embodiments, the hydrophobic group may be derived from a fatty alcohol such as stearyl alcohol, dodecyl alcohol or decyl alcohol. In other embodiments, is a hydrocarbon-based polymer such as polybutadiene.

When X and/or X' denote a group comprising a tertiary or quaternary amine, X and/or X' may be chosen from one of the following formulae:

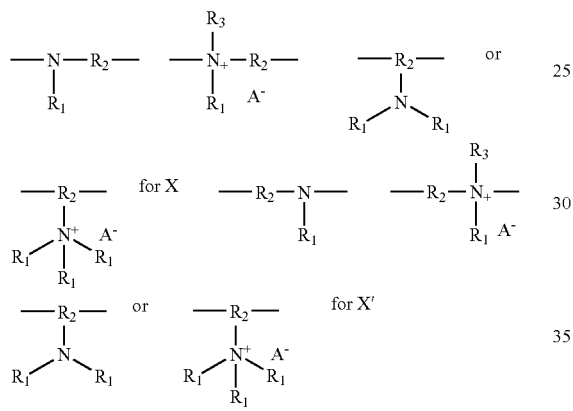

wherein:
each $R_2$ is independently chosen from a linear or branched alkylene radical having from 1 to 20 carbon atoms, optionally comprising a saturated or unsaturated ring, and an arylene radical, and wherein at least one of the carbon atoms is optionally replaced with a heteroatom chosen from N, S, O, and P;

each $R_1$ and $R_3$, which may be identical or different, is chosen from a linear or branched $C_1$-$C_{30}$ alkyl or alkenyl radical and an aryl radical, and wherein at least one of the carbon atoms is optionally replaced with a heteroatom chosen from N, S, O, and P; and $A^-$ is a physiologically acceptable counterion.

The groups L, L' and L" represent a group derived from a diisocyanate of the formula:

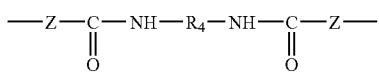

wherein:
each Z is independently chosen from —O—, —S—, and —NH—; and $R_4$ is chosen from a linear or branched alkylene radical having from 1 to 20 carbon atoms, optionally comprising a saturated or unsaturated ring, and an arylene radical, and wherein at least one of the carbon atoms is optionally replaced with a heteroatom chosen from N, S, O, and P.

The groups P and P' comprising an amine function may independently be chosen from at least one of the following formulae:

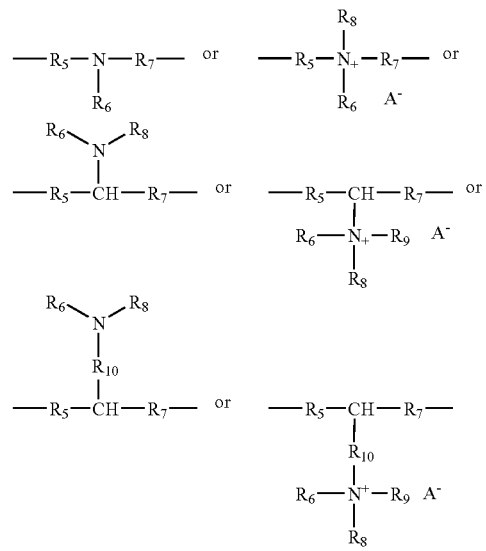

wherein:
$R_5$ and $R_7$, which may be identical or different, are each chosen from a linear or branched alkylene radical having from 1 to 20 carbon atoms, optionally comprising a saturated or unsaturated ring, and an arylene radical, and wherein at least one of the carbon atoms is optionally replaced with a heteroatom chosen from N, S, O, and P;

$R_6$, $R_8$ and $R_9$, which may be identical or different, are each chosen from a linear or branched $C_1$-$C_{30}$ alkyl or alkenyl radical and an aryl radical, and wherein at least one of the carbon atoms is optionally replaced with a heteroatom chosen from N, S, O, and P;

$R_{10}$ is a linear or branched, optionally unsaturated alkylene group optionally comprising one or more heteroatoms chosen from N, O, S and P; and $A^-$ is a physiologically acceptable counterion.

With respect to the meaning of Y, the term "hydrophilic group" means a polymeric or non-polymeric water-soluble group.

As an example, when the hydrophilic group is not a polymer, it may be chosen from, for example, ethylene glycol, diethylene glycol, and propylene glycol.

When the hydrophilic group is a hydrophilic polymer, it may be, for example, chosen from of polyethers, sulfonated polyesters, sulfonated polyamides, or a mixture of these polymers. In at least one embodiment, the hydrophilic compound is a polyether, such as a poly(ethylene oxide) or poly(propylene oxide).

The cationic associative polyurethanes of formula (IV) may be formed from diisocyanates and from various compounds with functions comprising a labile hydrogen. The functions comprising a labile hydrogen may be alcohol, primary or secondary amine, or thiol moieties, giving, after reaction with the diisocyanate moieties, polyurethanes, polyureas and polythioureas, respectively. The term "polyurethanes," as used herein, encompasses several types of polymers: polyurethanes per se, polyureas, and polythioureas, and also copolymers thereof.

The first type of compound involved in the preparation of polyurethanes of formula (IV) is a compound comprising at least one unit containing an amine function. The compound may be multifunctional, for example, difunctional. In some embodiments, the compound comprises two labile hydrogen atoms borne, for example, by a hydroxyl, primary amine, secondary amine, or thiol function. A mixture of multifunctional and difunctional compounds in which the percentage of multifunctional compounds is low may also be used.

These types of compounds may be represented by one of the following formulae:

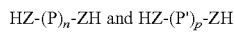

$$HZ\text{-}(P)_n\text{-}ZH \text{ and } HZ\text{-}(P')_p\text{-}ZH$$

wherein Z, P, P', n, and p are as defined above.

Examples of compounds containing an amine function include, but are not limited to, N-methyldiethanolamine, N-tert-butyldiethanolamine, and N-sulfoethyldi-ethanolamine.

The second type of compound involved in the preparation of polyurethanes of formula (IV) is a diisocyanate of the formula:

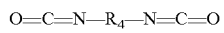

$$O\text{=}C\text{=}N\text{—}R_4\text{—}N\text{=}C\text{=}O$$

wherein $R_4$ is as defined above.

Examples of such compounds include, but are not limited to, methylenediphenyl diisocyanate, methylenecyclohexane diisocyanate, isophorone diisocyanate, toluene diisocyanate, naphthalene diisocyanate, butane diisocyanate, and hexane diisocyanate.

A third type of compound involved in the preparation of the polyurethanes of formula (IV) is a hydrophobic compound intended to form the terminal hydrophobic groups of the polymer of formula (IV).

These compounds comprise hydrophobic groups and functions comprising a labile hydrogen, for example a hydroxyl, primary or secondary amine, or thiol function.

Examples of such compounds include, but are not limited to, fatty alcohols such as stearyl alcohol, dodecyl alcohol, and decyl alcohol. When these compounds comprise a polymeric chain, it may be, for example, α-hydroxylated hydrogenated polybutadiene.

The hydrophobic group of the polyurethane of formula (IV) may also be formed from the quaternization reaction of a tertiary amine of a compound comprising at least one tertiary amine unit. Thus, the hydrophobic group is introduced via the quaternizing agent. The quaternizing agent is a compound of the formula RQ or R'Q, wherein R and R' are as defined above and Q is a leaving group such as a halide, a sulfate, etc.

The cationic associative polyurethane may also comprise a hydrophilic block. This block may be formed from a fourth type of compound involved in the preparation of the polymer. This compound may be multifunctional, for example, difunctional. It is also possible to have a mixture with a low percentage of multifunctional compound.

The functions comprising a labile hydrogen may be alcohol, primary or secondary amine or thiol functions. The compound may be a polymer terminated at the chain ends with one of these functions comprising a labile hydrogen.

For example, when the compound is not a polymer, it may be chosen from ethylene glycol, diethylene glycol, and propylene glycol.

When it is a hydrophilic polymer, the compound may be chosen from, for example, polyethers, sulfonated polyesters and sulfonated polyamides, or a mixture of these polymers. The hydrophilic compound may be a polyether, such as poly (ethylene oxide) or poly(propylene oxide).

The hydrophilic group termed Y in formula (IV) is optional. Specifically, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group may be used.

(II) Quaternized cellulose derivatives and polyacrylates containing non-cyclic amine side groups may also be used. Quaternized cellulose derivatives include, but are not limited to, quaternized celluloses modified with groups comprising at least one fatty chain, such as alkyl, arylalkyl or alkylaryl groups containing at least 8 carbon atoms, and mixtures thereof; and quaternized hydroxyethylcelluloses modified with groups comprising at least one fatty chain, such as alkyl, arylalkyl or alkylaryl groups containing at least 8 carbon atoms, and mixtures thereof.

The alkyl radicals borne by the above quaternized celluloses or hydroxyethylcelluloses may have from 8 to 30 carbon atoms. Examples of aryl radicals include phenyl, benzyl, naphthyl, and anthryl groups.

Examples of quaternized alkylhydroxyethylcelluloses having $C_8$-$C_{30}$ fatty chains include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

(III) Cationic polyvinyllactams described in patent application FR-01/01 106 (now published as FR 2 820 032) may also be used.

The polymers comprise:
(a) at least one vinyllactam or alkylvinyllactam monomer, and
(b) at least one monomer of formula (V) or (VI) below:

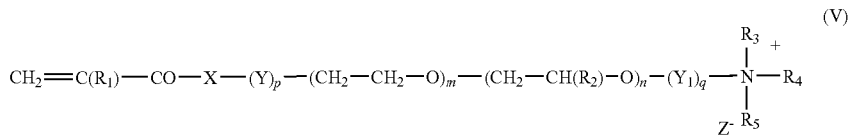

$$CH_2\text{=}C(R_1)\text{—}CO\text{—}X\text{—}(Y)_p\text{—}(CH_2\text{—}CH_2\text{—}O)_m\text{—}(CH_2\text{—}CH(R_2)\text{—}O)_n\text{—}(Y_1)_q\text{—}\underset{Z^-}{\overset{R_3}{\underset{|}{\overset{|}{N^+}}}}\text{—}R_4 \quad (V)$$
$$\phantom{CH_2\text{=}C(R_1)\text{—}CO\text{—}X\text{—}(Y)_p\text{—}(CH_2\text{—}CH_2\text{—}O)_m\text{—}(CH_2\text{—}CH(R_2)\text{—}O)_n\text{—}(Y_1)_q\text{—}} R_5$$

-continued

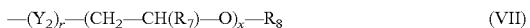
(VI)

wherein:
X is independently chosen from an oxygen atom and a radical $NR_6$,
$R_1$ and $R_6$, which may be identical or different, are chosen from a hydrogen atom and a linear or branched $C_1$-$C_5$ alkyl radical,
$R_2$ is a linear or branched $C_1$-$C_4$ alkyl radical,
$R_3$, $R_4$ and $R_5$, which may be identical or different, are each chosen from a hydrogen atom, a linear or branched $C_1$-$C_{30}$ alkyl radical, and a radical of formula (VII):

$$—(Y_2)_r—(CH_2—CH(R_7)—O)_x—R_8 \quad (VII)$$

wherein Y, $Y_1$ and $Y_2$, which may be identical or different, are each chosen from a linear or branched $C_2$-$C_{16}$ alkylene radical,
$R_7$ is chosen from a hydrogen atom, a linear or branched $C_1$-$C_4$ alkyl radical, and a linear or branched $C_1$-$C_4$ hydroxyalkyl radical,
$R_8$ is chosen from a hydrogen atom and a linear or branched $C_1$-$C_{30}$ alkyl radical,
p, q and r, which may be identical or different, are each chosen from 0 and 1,
m and n, which may be identical or different, are each chosen from an integer ranging from 0 to 100,
x is an integer ranging from 1 to 100, and
$Z^-$ is chosen from an organic and mineral acid anion, with the provisos:
at least one of the substituents $R_3$, $R_4$, $R_5$ or $R_8$ is a linear or branched $C_9$-$C_{30}$ alkyl radical,
if m or n is other than zero, then q is equal to 1, and
if m or n is equal to zero, then p or q is equal to 0.

The cationic poly(vinyllactam) polymers may be crosslinked or non-crosslinked and may also be block polymers.

In at least one embodiment, the counterion $Z^-$ of the monomers of formula (V) is chosen from halide ions, phosphate ions, methosulfate ion, and tosylate ion.

In at least one embodiment, $R_3$, $R_4$ and $R_5$ denote, independently of each other, a hydrogen atom or a linear or branched $C_1$-$C_{30}$ alkyl radical.

In at least one embodiment, the monomer (b) is a monomer of formula (V), and for example, m and n may be equal to 0.

The vinyllactam or alkylvinyllactam monomer may be a compound of formula (VIII):

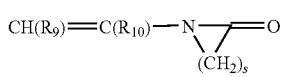
(VIII)

wherein:
s is an integer ranging from 3 to 6,
$R_9$ is chosen from a hydrogen atom and a $C_1$-$C_5$ alkyl radical, and
$R_{10}$ is chosen from a hydrogen atom and a $C_1$-$C_5$ alkyl radical, with the proviso that at least one of $R_9$ and $R_{10}$ is a hydrogen atom.

In at least one embodiment, the monomer (VII) is vinylpyrrolidone.

The cationic poly(vinyllactam) polymers may further comprise at least one additional monomer, such as cationic or nonionic monomers.

Compounds that may be used include the following terpolymers comprising at least:
(a) one monomer of formula (VIII),
(b) one monomer of formula (V) wherein p=1, q=0, $R_3$ and $R_4$, which may be identical or different, are each chosen from a hydrogen atom and a $C_1$-$C_5$ alkyl radical, and $R_5$ is a $C_9$-$C_{24}$ alkyl radical, and
(c) one monomer of formula (VI) wherein $R_3$ and $R_4$ which may be identical or different, are each chosen from a hydrogen atom and a $C_1$-$C_5$ alkyl radical.

In some embodiments, terpolymers comprising from 40% to 95% of monomer (a), from 0.1% to 55% of monomer (c), and from 0.25% to 50% of monomer (b) may be used.

Such polymers are described, for example, in patent application WO 00/68282, which is hereby incorporated by reference.

Cationic poly(vinyllactam) polymers that may be used include, but ate not limited to, vinylpyrrolidone/dimethylaminopropylmethacrylamide/dodecyldimethylmethacrylamidopropylammonium tosylate terpolymers, vinyl pyrrolidone/dimethylamino-propylmethacrylamide/cocoyldimethylmethacrylamidopropylammonium tosylate terpolymers, vinylpyrrolidone/dimethylaminopropylmethacrylamide/lauryldimethylmethacrylamidopropyl-ammonium tosylate, and chloride terpolymers.

The weight-average molecular mass of the cationic poly (vinyllactam) polymers may range from 500 to 20,000,000, such as from 200,000 to 2,000,000 or from 400,000 to 800,000.

Amphoteric Associative Polymers

The amphoteric associative polymers may be chosen from those comprising at least one non-cyclic cationic unit. For example, the polymers may be prepared from or comprise from 1 mol % to 20 mol %, such as from 1.5 mol % to 15 mol % or from 1.5 mol % to 6 mol %, of monomer comprising a fatty chain, relative to the total number of moles of monomers.

Amphoteric associative polymers that may be used comprise, or may be prepared by copolymerizing:
(1) at least one monomer of formula (IXa) or (IXb):

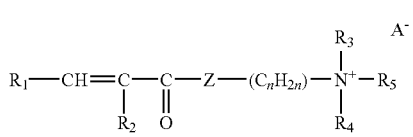
(IXa)

-continued

wherein:
R$_1$ and R$_2$, which may be identical or different, are each chosen from a hydrogen atom and a methyl radical,
R$_3$, R$_4$ and R$_5$, which may be identical or different, are each chosen from a linear or branched alkyl radical having from 1 to 30 carbon atoms,
Z is chosen from an NH group and an oxygen atom,
n is an integer ranging from 2 to 5, and
A$^-$ is an anion derived from an organic or mineral acid, such as a methosulfate anion or a halide such as chloride or bromide;

(2) at least one monomer of formula (X):

$$R_6\text{---}CH\!=\!CR_7\text{---}COOH \quad (X)$$

wherein:
R$_6$ and R$_7$, which may be identical or different, are each chosen from a hydrogen atom and a methyl radical; and (3) at least one monomer of formula (XI):

$$R_6\text{---}CH\!=\!CR_7\text{---}COXR_8 \quad (XI)$$

wherein:
R$_6$ and R$_7$, which may be identical or different, are each chosen from a hydrogen atom and a methyl radical,
X is chosen from an oxygen or nitrogen atom, and
R$_8$ is a linear or branched alkyl radical having from 1 to 30 carbon atoms; and wherein at least one of the monomers of formula (IXa), (IXb) or (XI) comprises at least one fatty chain.

In at least one embodiment, the monomers of formulae (IXa) and (IXb) are chosen from dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, and dimethylaminopropylmethacrylamide, dimethylaminopropylacrylamide. These monomers are optionally quaternized, for example with a C$_1$-C$_4$ alkyl halide or a C$_1$-C$_4$ dialkyl sulfate.

In at least one embodiment, the monomer of formula (IXa) may be chosen from acrylamidopropyltrimethylammonium chloride and methacrylamidopropyltrimethylammonium chloride.

In at least one embodiment, the monomers of formula (X) may be chosen from acrylic acid, methacrylic acid, crotonic acid and 2-methylcrotonic acid, for example, acrylic acid.

In at least one embodiment, the monomers of formula (XI) may be chosen from C$_{12}$-C$_{22}$ alkyl acrylates and methacrylates, for example, C$_{16}$-C$_{18}$ alkyl acrylates and methacrylates.

In at least one embodiment, the monomers constituting the fatty-chain amphoteric polymers may be already neutralized and/or quaternized.

In at least one embodiment, the ratio of the number of cationic charges/anionic charges is equal to 1.

The amphoteric associative polymers according to the present disclosure may comprise from 1 mol % to 10 mol % of the monomer comprising a fatty chain (monomer of formula (IXa), (IXb) or (XI)), for example, from 1.5 mol % to 6 mol %.

The weight-average molecular weights of the amphoteric associative polymers may range from 500 to 50,000,000, for example, from 10,000 to 5,000,000.

The amphoteric associative polymers may further comprise other monomers such as nonionic monomers, for example, C$_1$-C$_4$ alkyl acrylates or methacrylates.

Amphoteric associative polymers are described and prepared, for example, in patent application WO 98/44012.

In some embodiments, the amphoteric associative polymers are acrylic acid/(meth)acrylamidopropyltrimethylammonium chloride/stearyl methacrylate terpolymers.

Nonionic Associative Polymers

In at least one embodiment, the nonionic associative polymers useful herein are chosen from:

(1) celluloses modified with groups comprising at least one fatty chain; examples include:
hydroxyethylcelluloses modified with groups comprising at least one fatty chain, such as alkyl, arylalkyl, and alkylaryl groups, and mixtures thereof, for example, with C$_8$-C$_{22}$ alkyl groups, for example the product Natrosol Plus Grade 330 CS® (C$_{16}$ alkyls) sold by the company Aqualon, and the product Bermocoll EHM 100® sold by the company Berol Nobel,
celluloses modified with alkylphenyl polyalkylene glycol ether groups, such as the product Amercell Polymer HM-1500® (nonylphenyl polyethylene glycol (15) ether) sold by the company Amerchol;

(2) hydroxypropyl guars modified with groups comprising at least one fatty chain, such as the product Esaflor HM 22® (C$_{22}$ alkyl chain) sold by the company Lamberti, and the products RE210-18® (C$_{14}$ alkyl chain) and RE205-1® (C$_{20}$ alkyl chain) sold by the company Rhône-Poulenc;

(3) copolymers comprised of vinylpyrrolidone and fatty-chain hydrophobic monomers such as the products Antaron V216® and Ganex V216® (vinylpyrrolidone/hexadecene copolymer) sold by the company I.S.P., and the products Antaron V220® and Ganex V220® (vinylpyrrolidone/eicosene copolymer) sold by the company I.S.P.;

(4) copolymers of C$_1$-C$_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®;

(5) copolymers of hydrophilic methacrylates or acrylates and of hydrophobic monomers comprising at least one fatty chain, such as, polyethylene glycol methacrylate/lauryl methacrylate copolymer;

(6) polyurethane polyethers comprising both hydrophilic blocks (e.g., polyoxyethylenated) and hydrophobic blocks which may be aliphatic sequences alone and/or cycloaliphatic and/or aromatic sequences; and (7) polymers with an aminoplast ether skeleton comprising at least one fatty chain, such as the Pure Thix® compounds sold by the company Sud-Chemie.

In at least one embodiment, the polyurethane polyethers comprise at least two hydrocarbon-based lipophilic chains having from 6 to 30 carbon atoms, separated by a hydrophilic block, the hydrocarbon-based chains possibly being pendent chains or chains at the end of a hydrophilic block. For example, it is possible for one or more pendent chains to be included. In addition, the polymer may comprise a hydrocarbon-based chain at one end or at both ends of a hydrophilic block.

The polyurethane polyethers may be multiblock, for example, in triblock form. Hydrophobic blocks may be at each end of the chain (for example, a triblock copolymer with a hydrophilic central block) or distributed both at the ends and in the chain (for example, a multiblock copolymer). These polymers may also be graft polymers or starburst polymers.

The nonionic fatty-chain polyurethane polyethers may be triblock copolymers in which the hydrophilic block is a polyoxyethylenated chain having from 50 to 1000 oxyethylene groups. The nonionic polyurethane polyethers comprise a urethane linkage between the hydrophilic blocks.

Nonionic fatty-chain polyurethane polyethers also include those in which the hydrophilic blocks are linked to the lipophilic blocks via other chemical bonds.

Examples of fatty-chain nonionic polyurethane polyethers include Rheolate 205®, which has a urea function, sold by the company Rheox, and Rheolate® 208, 204 and 212, and Acrysol RM 184®.

Other examples include the product Elfacos T210® having a $C_{12-14}$ alkyl chain, and the product Elfacos T212® having a $C_{18}$ alkyl chain, from Akzo.

The product DW 1206B® from Rohm & Haas having a $C_{20}$ alkyl chain and a urethane linkage, sold at a solids content of 20% in water, may also be used.

It is also possible to use solutions and dispersions of these polymers, for example, in water or in aqueous-alcoholic media. Examples of such polymers are Rheolate® 255, Rheolate® 278 and Rheolate® 244 sold by the company Rheox. The products DW 1206F and DW 1206J sold by the company Rohm & Haas may also be used.

Polyurethane polyethers that may be used are described in the article by G. Fonnum, J. Bakke and Fk. Hansen—Colloid Polym. Sci 271, 380-389 (1993).

In some embodiments, polyurethane polyethers that may be obtained by polycondensation of at least three compounds comprising (i) at least one polyethylene glycol having from 150 to 180 mol of ethylene oxide, (ii) stearyl alcohol or decyl alcohol, and (iii) at least one diisocyanate, are used.

Such polyurethane polyethers are sold by the company Rohm & Haas under the names Aculyn 46® and Aculyn 44®. Aculyn 46® is a polycondensate of polyethylene glycol having 150 or 180 mol of ethylene oxide, of stearyl alcohol and of methylene-bis(4-cyclohexyl isocyanate) (SMDI), at 15% by weight in a matrix of maltodextrin (4%) and water (81%). Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%).

In at least one embodiment, the associative polymers are chosen from nonionic and cationic polymers, for example, from polyether polyurethanes comprising hydrophilic and hydrophobic blocks, polymers with an aminoplast ether backbone comprising at least one fatty chain, cationic associative polyurethanes, quaternized cellulose derivatives comprising at least one fatty chain, and cationic polyvinyllactams.

According to certain embodiments, the associative polymers are chosen from quaternized ($C_8$-$C_{30}$)alkylhydroxyethylcelluloses, for example, quaternized laurylhydroxyethylcellulose.

The concentration of associative polymers in the compositions may range from 0.01% to 10% by weight, for example, from 0.1% to 5% by weight, relative to the total weight of the compositions.

Peroxygenated Salts

Peroxygenated salts may be chosen, for example, from alkali metal and alkaline-earth metal persulfates, perborates, percarbonates and peroxides, and mixtures thereof. In some embodiments, persulfates and mixtures thereof are used, for example sodium, potassium and ammonium persulfates, and mixtures thereof.

The concentration of peroxygenated salts in the compositions disclosed herein may range from 1% to 70% by weight, for example, from 20% to 60% by weight, relative to the total weight of the compositions.

Alkaline Agents

Alkaline agents that may be used include, for example, urea, ammonium salts, for example, ammonium chloride, ammonium sulfate, ammonium, phosphate, and ammonium nitrate; silicates, phosphates and carbonates of alkali metals or of alkaline-earth metals such as lithium, sodium, potassium, magnesium, calcium or barium; and mixtures thereof. In at least one embodiment, the alkaline agents are chosen from ammonium chloride and silicates and carbonates, and mixtures thereof.

The concentration of alkaline agents in the compositions may range from 0.01% to 40% by weight, for example, from 0.1% to 30% by weight, relative to the total weight of the composition.

According to at least one embodiment, the composition is in the form of a paste and may further comprise at least one inert organic liquid phase.

As used herein, the term "liquid phase" means any phase capable of flowing at room temperature, generally from 15° C. to 40° C., and at atmospheric pressure, under the action of its own weight.

As used herein, the term "inert organic liquid" means an organic liquid that is chemically inert with respect to hydrogen peroxide. A liquid is inert if the degradation of hydrogen peroxide in the presence of this liquid is less than 25% after 15 hours at 100° C.

Examples of inert liquid phases include polydecenes of formula $C_{10n}H_{[(20n)+2]}$ wherein n ranges from 3 to 9, for example, from 3 to 7; esters of fatty alcohols or of fatty acids; sugar esters or diesters of $C_{12}$-$C_{24}$ fatty acids; cyclic ethers or cyclic esters; silicone oils; mineral oils; plant oils; and mixtures thereof.

Compounds of formula $C_{10n}H_{[(20n)+2]}$ wherein n ranges from 3 to 9 correspond to the name "polydecene" of the CTFA dictionary, 7th edition, 1997 of the Cosmetic, Toiletry and Fragrance Association, USA, and also to the same INCI name in the USA and in Europe. These are poly-1-decene hydrogenation products.

In some embodiments, n ranges from 3 to 7.

Examples include the products sold under the name Silkflo® 366 NF Polydecene by the company Amoco Chemical, and those sold under the name Nexbase® 2002 FG, 2004 FG, 2006 FG and 2008 FG by the company Fortum.

Examples of esters of fatty alcohols and of fatty acids include esters of saturated, linear or branched $C_3$-$C_6$ lower monoalcohols with monofunctional $C_{12}$-$C_{24}$ fatty acids. The fatty acids may be linear or branched, saturated or unsaturated, for example, chosen from oleates, laurates, palmitates, myristates, behenates, cocoates, stearates, linoleates, linolenates, caprates and arachidonates, and mixtures thereof, for example, oleo-palmitates, oleo-stearates, and palmito-stearates.

Examples of these esters include:
- isopropyl palmitate, isopropyl myristate and octyidodecyl stearate,
- esters of linear or branched $C_3$-$C_8$ monoalcohols with difunctional $C_8$-$C_{24}$ fatty acids, the fatty acids possibly being linear or branched, and saturated or unsaturated, for example, the isopropyl diester of sebacic acid, also known as diisopropyl sebacate,
- esters of linear or branched $C_3$-$C_8$ monoalcohols with difunctional $C_2$-$C_8$ fatty acids, the fatty acids possibly being linear or branched, and saturated or unsaturated, for example, dioctyl adipate and dicaprylyl maleate, and
- esters of trifunctional acids, for example, triethyl citrate.

With respect to the sugar esters and diesters of $C_{12}$-$C_{24}$ fatty acids, the term "sugar" means compounds comprising several alcohol functions, with or without an aldehyde or ketone function, and which comprise at least 4 carbon atoms. These sugars may be monosaccharides, oligosaccharides or polysaccharides.

Sugars that may be used include, but are not limited to, sucrose (or saccharose), glucose, galactose, ribose, fucose, maltose, fructose, mannose, arabinose, xylose, lactose, and derivatives thereof, for example, alkyl derivatives such as methyl derivatives, e.g., methylglucose.

Sugar esters of fatty acids that may be used may be chosen from esters and mixtures of esters of sugars described above and of linear or branched, saturated, and unsaturated $C_{12}$-$C_{24}$ fatty acids.

The esters may be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates, arachidonates, and mixtures thereof such as, oleo-palmitate, oleo-stearate, and palmito-stearate mixed esters.

In some embodiments, monoesters and diesters are used, for example, sucrose, glucose or methylglucose, mono- or dioleates, stearates, behenates, oleopalmitates, linoleates, linolenates, and oleostearates.

An example is the product sold under the name Glucate® DO by the company Amerchol, which is a methylglucose dioleate.

Examples of esters or mixtures of esters of sugar and of fatty acid also include:
- products sold under the names F160, F140, F110, F90, F70 and SL 40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- products sold under the name Ryoto Sugar Esters, for example, referenced B370 and corresponding to sucrose behenate formed from 20% monoester and 80% di- and triester-polyester; and
- sucrose mono-dipalmito-stearate sold by the company Goldschmidt under the name Tegosoft® PSE.

Cyclic ethers and cyclic esters include, but are not limited to, γ-butyrolactone, dimethyl isosorbide, and diisopropyl isosorbide.

Silicone oils may also be used as an inert organic liquid phase.

Suitable silicone oils include liquid, non-volatile silicone fluids with a viscosity of less than or equal to 10,000 mPa·s at 25° C., the viscosity of the silicones measured according to ASTM standard 445 Appendix C.

Silicone oils are defined in greater detail in Walter Noll's "Chemistry and Technology of Silicones" (1968)—Academic Press.

Silicone oils that may be used include, but are not limited to, the silicone oils sold under the names DC-200 Fluid—5 mPa·s, DC-200 Fluid—20 mPa·s, DC-200 Fluid—350 mPa·s, DC-200 Fluid—1000 mPa·s and DC-200 Fluid—10 000 mPa·s by the company Dow Corning.

Mineral oils may also be used as an inert organic liquid phase, for example liquid paraffin.

Plant oils may also be used, for example, avocado oil, olive oil, and liquid jojoba wax.

The inert organic liquid phase may be chosen from polydecenes of the formula $C_{10n}H_{[(20n)+2]}$ wherein n ranges from 3 to 9, for example, from 3 to 7, esters of fatty alcohols or of fatty acids, and mixtures thereof.

When the compositions comprise at least one inert organic liquid phase, the content of inert organic liquid phase may range from 5% to 60% by weight, for example, from 10% to 50% or from 15% to 45% by weight, relative to the weight of the anhydrous paste.

In at least one embodiment, the compositions disclosed herein are anhydrous.

As used herein, a composition is anhydrous when it has a water content of less than 1% by weight, for example, less than 0.5% by weight relative to the total weight of the composition.

According to another embodiment, the compositions are aqueous. They may then also comprise hydrogen peroxide.

In this case, the compositions are ready to use and result from the mixing of an anhydrous composition with an aqueous composition optionally comprising hydrogen peroxide. The pH generally ranges from 3 to 11, for example, from 7 to 11.

The compositions may also further comprise various additives conventionally used in cosmetics.

The compositions may thus comprise mineral or organic thickeners, fillers such as clays, binders such as vinylpyrrolidone, lubricants, for example, polyol stearates or alkali metal or alkaline-earth metal stearates, hydrophilic or hydrophobic silicas, pigments, dyes other than those described above, matting agents, for example, titanium oxides or anionic, nonionic, cationic, amphoteric or zwitterionic surfactants, antioxidants, penetrants, sequestrants, buffers, dispersants, film-forming agents, preserving agents, opacifiers, vitamins, fragrances, anionic, cationic, nonionic, amphoteric or zwitterionic polymers, ceramides, and conditioning agents, for example, volatile or non-volatile, modified or unmodified silicones.

When the compositions comprise hydrogen peroxide, they may also comprise agents for controlling the release of oxygen, such as magnesium carbonate or oxide.

The additives and the agents for controlling the release of oxygen as defined above may be present in an amount for each ranging from 0.01% to 40% by weight, for example, from 0.1% to 30% by weight, relative to the total weight of the composition.

A person skilled in the art will take care to select the optional additional compounds such that the advantageous properties intrinsically associated with the compositions disclosed herein are not, or are not substantially, adversely affected by the envisaged additions.

The simultaneous bleaching and dyeing processes disclosed herein comprise applying to keratin fibers an anhydrous composition as defined above in the presence of an aqueous composition optionally comprising hydrogen peroxide. The aqueous composition optionally comprising hydrogen peroxide may be added to the anhydrous composition at the time of use. It may also be applied simultaneously with or sequentially to the anhydrous composition.

The present disclosure also relates to a multi-compartment device, comprising at least two compositions, the mixing of which leads to an aqueous composition as described above.

According to at least one embodiment, the device comprises a first compartment containing a composition (A) comprising, in a suitable dyeing medium, at least one anionic or nonionic dye and at least one associative polymer as defined above, a second compartment containing an anhydrous composition (B) comprising at least one peroxygenated salt and at least one alkaline agent as defined above, and a third compartment containing an aqueous hydrogen peroxide composition (C).

According to other embodiments, the device comprises a first compartment containing a composition (D) comprising, in a suitable dyeing medium, at least one anionic or nonionic dye as defined above, a second compartment containing an anhydrous composition (E) comprising at least one associative polymer, at least one peroxygenated salt and at least one alkaline agent as defined above, and a third compartment containing an aqueous hydrogen peroxide composition (C).

According to yet other embodiments, the device comprises a first compartment containing an anhydrous composition (F) comprising at least one anionic or nonionic dye, at least one associative polymer, at least one peroxygenated salt and at least one alkaline agent as defined above, and a second compartment containing an aqueous hydrogen peroxide composition (C).

In at least one embodiment, the device comprises a first compartment containing an anhydrous composition (E) comprising at least one associative polymer, at least one peroxygenated salt and at least one alkaline agent as defined above, and a second compartment containing a composition (G) comprising, in a suitable dyeing medium, at least one anionic or nonionic dye as defined above and hydrogen peroxide.

According to other embodiments, the device comprises a first compartment containing an anhydrous composition (B) comprising at least one peroxygenated salt and at least one alkaline agent as defined above, and a second compartment containing a composition (H) comprising, in a suitable dyeing medium, at least one anionic or nonionic dye and at least one associative polymer as defined above and hydrogen peroxide.

The suitable dyeing medium for the compositions (A), (C), (D), (G) and (H) generally comprise water or of a mixture of water and of at least one organic solvent, for example, to dissolve the compounds that are not sufficiently water-soluble. Examples of organic solvents include $C_1$-$C_4$ lower alkanols such as ethanol and isopropanol; glycerol; glycols and glycol ethers, for example, 2-butoxyethanol, propylene glycol and propylene glycol monomethyl ether, and aromatic alcohols, for example, benzyl alcohol and phenoxy-ethanol, similar solvents, and mixtures thereof.

The solvents may be present in amounts, for example, ranging from 1% to 40% by weight, such as from 5% to 30% by weight, relative to the total weight of the dye composition.

Compositions (A) and (D), also known as "boosters", may be formulated at acidic, neutral or alkaline pH. In some embodiments, the pH ranges from 3 to 12, for example, from 4 to 11.

Compositions (C), (G) and (H) may have a pH of less than 7, the acidic pH ensuring the stability of the hydrogen peroxide in this composition.

Compositions (A), (C), (D), (G) and (H) may be in various forms, such as in the form of liquids, creams or gels, or in any other form that is suitable for dyeing keratin fibers.

The anhydrous compositions (B), (E) and (F) may be in the form of a powder or paste. When they are in the form of a paste, they also may comprise an inert organic liquid phase as defined above.

Compositions (A) to (H) may also contain various additives conventionally used in cosmetics, such as those described above.

Compositions (C), (G) and (H) may also comprise agents for controlling the release of oxygen as defined above.

The devices described herein may be equipped with a means for applying the desired mixture to the hair, such as the devices described in patent FR-2 586 913.

Using the devices, it is possible to simultaneously bleach and dye keratin fibers by means of the processes described above.

The present disclosure also relates to the use of the compositions described above for simultaneously bleaching and dyeing keratin fibers.

The invention is illustrated in greater detail by the example described below. Other than in the example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLE

The ready-to-use compositions below were prepared:

|  | Composition | | |
|---|---|---|---|
|  | A | B | C |
| 3-Methylamino-4-nitrophenoxyethanol | 0.5 g | — | — |
| 4-Amino-4'-nitroazobenzene or Disperse Orange 3 | — | 0.5 g | — |
| Sodium salt of 5-(2,4-dinitro-phenylamino)-2-(phenylamino) benzenesulfonic acid or Acid Orange 3 | — | — | 0.5 g |
| (Meth)acrylic acid/ethyl acrylate/behenyl methacrylate oxyethylenated (25 EO) terpolymer as an aqueous emulsion (Aculyn 28) | 1.3 g | 1.3 g | 1.3 g |
| Oxyethylenated (33 EO) cetylstearyl alcohol | 1.4 g | 1.4 g | 1.4 g |
| Cetylstearyl alcohol | 5.7 g | 5.7 g | 5.7 g |
| Ethylenediaminetetraacetic acid | 0.06 g | 0.06 g | 0.06 g |
| Potassium persulfate | 12 g | 12 g | 12 g |
| Sodium disilicate hydrate | 4.3 g | 4.3 g | 4.3 g |
| Sodium persulfate | 1.7 g | 1.7 g | 1.7 g |
| Isopropyl myristate | 6.2 g | 6.2 g | 6.2 g |
| Bleached beeswax | 0.3 g | 0.3 g | 0.3 g |
| Liquid petroleum jelly | 0.3 g | 0.3 g | 0.3 g |
| Titanium oxide (untreated anatase) | 0.3 g | 0.3 g | 0.3 g |
| Hexamethyl diisocyanate/poly-ethylene glycol polyoxyethylenated copolymer containing α-ω stearyl end groups (Nuvis FX 1100) | 0.6 g | 0.6 g | 0.6 g |
| Weakly crosslinked potato carboxymethyl starch (tuber starch), sodium salt | 0.6 g | 0.6 g | 0.6 g |
| Sodium lauryl sulfate | 1.1 g | 1.1 g | 1.1 g |
| Magnesium stearate | 0.6 g | 0.6 g | 0.6 g |
| Magnesium oxide | 0.6 g | 0.6 g | 0.6 g |
| Tetrasodium pyrophosphate decahydrate | 0.02 g | 0.02 g | 0.02 g |
| Etidronic acid, tetrasodium salt, as an aqueous 30% solution | 0.1 g | 0.1 g | 0.1 g |
| Hydrogen peroxide as an aqueous 50% solution (200-volumes aqueous hydrogen peroxide solution) | 13.7 g | 13.7 g | 13.7 g |
| Sodium salicylate | 0.02 g | 0.02 g | 0.02 g |
| Preserving agents | qs | qs | qs |
| pH agents | qs pH 9.9 | qs pH 9.9 | qs pH 9.9 |
| Deionized water | qs 100 g | qs 100 g | qs 100 g |

Each of the compositions A, B and C was applied to a lock of natural chestnut-brown hair at a temperature of 37° C. After a leave-on time of 40 minutes, the locks were rinsed, washed with a standard shampoo, rinsed again, and then dried.

The shades obtained are described in the table below.

|  | Composition | | |
|---|---|---|---|
|  | A | B | C |
| Shade | Strong golden light blonde | Coppery-beige blonde | Coppery-beige blonde |

What is claimed is:

1. A composition for simultaneously bleaching and dyeing keratin fibers, comprising:
   at least one direct dye chosen from anionic and nonionic dyes, with the exception of 7-(6'-methylphenylazo)-1-acetamido-3,6-disulfo-8-hydroxynaphthalene, ortho-nitroanilines substituted meta to the amino group, quinoline, quinoline derivatives, and addition salts thereof;
   and wherein said composition for simultaneously bleaching and dyeing keratin fibers further comprises
   at least one associative polymer chosen from nonionic polymers and cationic polymers;
   at least one inert organic liquid phase;
   at least one peroxygenated salt; and
   at least one alkaline agent wherein the composition is anhydrous.

2. The composition according to claim 1, wherein the at least one direct dye is an anionic dye chosen from acidic nitro direct dyes, acidic azo dyes, acidic azine dyes, acidic triarylmethane dyes, acidic indoamine dyes, and acidic natural dyes.

3. The composition according to claim 2, wherein the anionic dye is chosen from:

Acid Red 87
Sodium salt of 2,4-dinitro-1-naphthol-7-sulfonic acid
Acid Orange 3
Acid Yellow 9/Food Yellow 2
Direct Red 45/Food Red 13
Acid Black 52
Acid Yellow 36
Sodium salt of 1-hydroxy-2-(2',4'-xylyl-5-
sulfonatoazo)naphthalene-4-sulfonic acid/Food Red 1
Acid Red 14/Food Red 3/Mordant Blue 79
Acid Brown 4
Acid Orange 7/Pigment Orange 17/Solvent Orange 49
Food Yellow 3/Pigment Yellow 104
Acid Red 27/Food Red 9
Acid Orange 10/Food Orange 4
Acid Red 44
Acid Red 33/Food Red 12
Acid Red 184
Acid Violet 3
Sodium salt of 1-hydroxy-2-(4'-acetamidophenylazo)-8-
acetamidonaphthalene-3,6-disulfonic acid/Acid Violet
7/Food Red 11
Acid Red 135
Acid Yellow 27
Acid Yellow 23/Food Yellow 4
4'-(Sulfonato-2",4"-dimethyl)bis(2,6-phenylazo)-1,3-
dihydroxybenzene/Acid Orange 24
Sodium salt of 1-amino-2-(4'-nitrophenylazo)-7-phenylazo-
8-hydroxynaphthalene-3,6-disulfonic acid/Acid Black 1
(4-((4-Methylphenyl)sulfonyloxy)phenylazo)-2,2'-dimethyl-4-
((2-hydroxy-5,8-disulfonato)naphthylazo)biphenyl/Acid Red
111
Food Black 2
1-(4'-Sulfonatophenylazo)-4-((2"-hydroxy-3"-acetylamino-
6",8"-disulfonato)naphthylazo)-6-sulfonatonaphthalene
(tetrasodium salt)/Food Black 1
4-β-Hydroxyethylamino-3-nitrobenzenesulfonic acid
Acid Blue 9
Acid Violet 43
Acid Green 25
Sodium salt of 1-amino-4-cyclohexylamino-9,10-
anthraquinone-2-sulfonic acid/Acid Blue 62
Acid Blue 78
Sodium salt of 4-hydroxy-3-((2-methoxyphenyl)azo)-1-
naphthalenesulfonic acid/Acid Red 4
2-Piperidino-5-nitrobenzenesulfonic acid
2-(4'-N,N-(2"-Hydroxyethyl)amino-2'-nitro)-
anilinethanesulfonic acid
4-β-Hydroxyethylamino-3-nitrobenzenesulfonic acid
Acid Violet 49
Acid Blue 7
Acid Blue 156
Acid Blue 317
Sodium salt of 1,2-dihydroxy-3-sulfoanthraquinone/Mordant
Red 3
Sodium salt of 1-amino-9,10-dihydro-9,10-dioxo-4-
(phenylamino)-2-anthracenesulfonic acid/Acid Blue 25
Sodium salt of 4-hydroxy-3-((2-methoxyphenyl)azo)-1-
naphthalenesulfonic acid/Acid Red 4.

4. The composition according to claim 1, wherein the at least one direct dye is a nonionic dye chosen from nitrobenzene dyes, azo dyes, azomethine dyes, methine dyes, anthraquinone dyes, naphthoquinone dyes, benzoquinone dyes, phenothiazine dyes, indigoid dyes, xanthene dyes, phenanthridine dyes, phthalocyanin dyes, and triarylmethane-based dyes.

5. The composition according to claim 4, wherein the nonionic dye is chosen from 1-hydroxy-3-nitro-4-N-(γ-hydroxypropyl)aminobenzene; N-(β-hydroxyethyl)-amino-3-nitro-4-aminobenzene; 1-hydroxy-3-nitro-4-N-(β-hydroxyethyl)aminobenzene; 1,4-diamino-2-nitrobenzene; 1-amino-2-nitro-4-methylaminobenzene; N-β-hydroxyethyl)-2-nitro-para-phenylenediamine; 2-nitro-4-aminodiphenylamine; 1-amino-3-nitro-6-hydroxybenzene; 1-(β-aminoethyl) amino-2-nitro-4-(β-hydroxyethyloxy)benzene; 1-(β,γ-dihydroxypropyl)oxy-3-nitro-4-(β-hydroxyethyl)aminobenzene; 1-hydroxy-3-nitro-4-aminobenzene; 1-hydroxy-2-amino-4,6-dinitrobenzene; 1-methoxy-3-nitro-4-(β-hydroxyethyl) aminobenzene; 2-nitro-4'-hydroxydiphenylamine; 1-(β-hydroxyethyl)amino-2-methoxy-4-nitrobenzene; 1-amino-2-nitro-6-methylbenzene; 1-(β-hydroxyethyl)amino-2-hydroxy-4-nitrobenzene; N-(β-hydroxyethyl)-2-nitro-4-trifluoromethylaniline; 4-(β-hydroxyethyl)amino-3-nitrochlorobenzene; 4-(β-hydroxyethyl)amino-3-nitromethylbenzene; 4-(β,γ-dihydroxypropyl)amino-3-nitrotrifluoromethylbenzene; 1-(β-ureidoethyl)amino-4-nitrobenzene; 1-hydroxy-2-amino-5-nitrobenzene; 1-amino-2-[tris(hydroxymethyl)methyl]-amino-5-nitrobenzene; 1-(β-hydroxyethyl)amino-2-nitrobenzene; 4-(β-hydroxyethyl) amino-3-nitrobenzamide; 1-(β-hydroxyethyl)amino-4-N,N-bis(β-hydroxyethyl)amino-2-nitrobenzene; 1-(γ-hydroxypropyl)amino-4-N,N-bis(β-hydroxyethyl)amino-2-nitrobenzene; 1-(β-hydroxyethyl)amino-4-(N-methyl-N-β-hydroxyethyl)amino-2-nitrobenzene; 1-(β-hydroxyethyl) amino-4-(N-ethyl-N-β-hydroxyethy)amino-2-nitrobenzene; 1-(β,γ-dihydroxypropyl)amino-4-(N-ethyl-N-β-hydroxyethyl)amino-2-nitrobenzene; Disperse Orange 3; Disperse Red 17; Disperse Violet 4; Disperse Violet 8; Disperse Blue 1; Disperse Red 15; Solvent Violet 13; Solvent Violet 11; Disperse Blue 3; Disperse Blue 7; Disperse Red 11; Natural Brown 7; Disperse Black 9; Disperse Violet 15; Natural Orange 6; 2-hydroxy-3-methoxy-1,4-naphthoquinone; 3-hydroxy-2-methyl-1,4-naphthoquinone; 3-hydroxy-2-methyl-1,4-phthiocol; 3,6-dihydroxy-5-methoxy-p-toluquinone; 3,6-dihydroxy-5-methoxy-spinulosin; and HC Blue 14.

6. The composition according to claim 1, wherein the concentration of the at least one direct dye ranges from 0.0001% to 10% by weight relative to the total weight of the composition.

7. The composition according to claim 1, wherein the at least one associative polymer is nonionic and chosen from a polyether polyurethane comprising hydrophilic and hydrophobic blocks, and a polymer with an aminoplast ether backbone comprising at least one fatty chain.

8. The composition according to claim 1, wherein the at least one associative polymer is cationic and chosen from an associative polyurethane, a quaternized cellulose derivative comprising at least one fatty chain, and a cationic polyvinyllactam.

9. The composition according to claim 8, wherein the at least one associative polymer is a quaternized cellulose derivative comprising at least one fatty chain chosen from quaternized ($C_8$-$C_{30}$)alkylhydroxyethylcelluloses.

10. The composition according to claim 9, wherein the quaternized cellulose derivative comprising at least one fatty chain is quaternized laurylhydroxyethyl-cellulose.

11. The composition according to claim 1, wherein the concentration of the at least one associative polymer ranges from 0.01% to 10% by weight relative to the total weight of the composition.

12. The composition according to claim 1, wherein the at least one peroxygenated salt is chosen from alkali metal and alkaline-earth metal persulfates, perborates, percarbonates, and peroxides.

13. The composition according to claim 12, wherein the at least one peroxygenated salt is a persulfate.

14. The composition according to claim 13, wherein the at least one peroxygenated salt is chosen from sodium persulfate, potassium persulfate, and ammonium persulfate.

15. The composition according to claim 1, wherein the concentration of the at least one peroxygenated salt ranges from 1% to 70% by weight relative to the total weight of the composition.

16. The composition according to claim 1, wherein the at least one alkaline agent is chosen from urea, ammonium chloride, ammonium sulfate, ammonium phosphate, ammonium nitrate, alkali metal silicates, alkaline-earth metal silicates, phosphates, and carbonates.

17. The composition according to claim 1, wherein the concentration of the at least one alkaline agent ranges from 0.01% to 40% by weight relative to the total weight of the composition.

18. The composition according to claim 1, wherein the at least one inert organic liquid phase is chosen from polydecenes of the formula $C_{10n}H_{[(20n)+2]}$ wherein n ranges from 3 to 9, fatty alcohol esters, fatty acid esters, $C_{12}$-$C_{24}$ fatty acid sugar esters, $C_{12}$-$C_{24}$ fatty acid diesters, cyclic ethers, cyclic esters, silicone oils, mineral oils, and plant oils.

19. The composition according to claim 1, wherein the at least one inert organic liquid phase is chosen from polydecenes of formula $C_{10n}H_{[(20n)+2]}$ wherein n ranges from 3 to 9, fatty alcohol esters, and fatty acid esters.

20. The composition according to claim 1, wherein the concentration of the at least one inert organic liquid phases ranges from 5% to 60% by weight relative to the total weight of the composition.

21. The composition according to claim 1, further comprising hydrogen peroxide.

22. A process for simultaneously bleaching and dyeing keratin fibers, comprising applying to the keratin fibers for simultaneously bleaching and dyeing an anhydrous composition in the presence of an aqueous composition optionally comprising hydrogen peroxide:

said anhydrous composition comprising:
at least one direct dye chosen from anionic and nonionic dyes, with the exception of 7-(6'-methylphenylazo)-1-acetamido-3,6-disulfo-8-hydroxynaphthal-ene, ortho-nitroanilines substituted meta to the amino group, quinoline, quinoline derivatives, and addition salts thereof,
at least one associative polymer chosen from nonionic polymers and cationic polymers,
at least one inert organic liquid phase,
at least one peroxygenated salt, and
at least one alkaline agent.

23. A multi-compartment device, comprising:
a first compartment comprising a first composition, and
a second compartment comprising a second composition, wherein the mixing of the first composition and the second composition results in an aqueous composition for simultaneously bleaching and dyeing keratin fibers, comprising:
at least one direct dye chosen from anionic and nonionic dyes, with the exception of 7-(6'-methylphenylazo)-1-acetamido-3,6-disulfo-8-hydroxynaphthalene, ortho-nitroanilines substituted meta to the amino group, quinoline, quinoline derivatives, and addition salts thereof;
at least one associative polymer chosen from nonionic polymers and cationic polymers;
at least one inert organic liquid phase;
at least one peroxygenated salt;
at least one alkaline agent; and
optionally hydrogen peroxide wherein at least one of the first or second composition is anhydrous.

* * * * *

UNITED STATES PATENT AND TRADEMARK OFFICE
CERTIFICATE OF CORRECTION

PATENT NO. : 7,799,092 B2 Page 1 of 1
APPLICATION NO. : 11/476875
DATED : September 21, 2010
INVENTOR(S) : Sylvain Kravtchenko It is certified that error appears in the above-identified patent and that said Letters Patent is hereby corrected as shown below:

On the Title Page, Item (74), in the "*Attorney, Agent, or Firm*", line 2,
"Farrabow," should read --Farabow,--.

On the Title Page, Item (57), in the Abstract, lines 4-5,
"7-(6'-methylphenylazo)-1-acetamido-3,6-dis-ulfo-8-hydroxynaph-thalene,"
should read
--7-(6'-methylphenylazo)-1-acetamido-3,6-disulfo-8-hydroxynaphthalene,--.

In claim 5, column 26, lines 20-21,
"1-(β-hydroxyethyl)amino-4-(N-ethyl-N-β-hydroxyethy)amino-2-nitrobenzene;"
should read
--1-(β-hydroxyethyl)amino-4-(N-ethyl-N-β-hydroxyethyl)amino-2-nitrobenzene;--.

In claim 10, column 26, line 53, "laurylhydroxyethyl-cellulose." should read
--laurylhydroxyethylcellulose.--.

In claim 22, column 28, lines 3-4,
"7-(6'-methylphenylazo)-1-acetamido-3,6-disulfo-8-hydroxynaphthal-ene,"
should read
--7-(6'-methylphenylazo)-1-acetamido-3,6-disulfo-8-hydroxynaphthalene,--.

Signed and Sealed this

Twenty-first Day of December, 2010

David J. Kappos
*Director of the United States Patent and Trademark Office*